United States Patent

Clavelle

[11] Patent Number: 5,675,840
[45] Date of Patent: Oct. 14, 1997

[54] SKIN HEAT SHIELD SYSTEM

[76] Inventor: Stella L. Clavelle, 3824 Deercreek La., Harvey, La. 70058

[21] Appl. No.: 633,681

[22] Filed: Apr. 17, 1996

[51] Int. Cl.⁶ .................................................. A42B 1/06
[52] U.S. Cl. ........................... 2/174; 2/209; 2/DIG. 11
[58] Field of Search ..................... 2/174, 209, 209.12, 2/DIG. 11, 7, 8, 195.1, 195.7, 200.1, 181, 172, 209.11, 423

[56] References Cited

U.S. PATENT DOCUMENTS

| | | | |
|---|---|---|---|
| 1,851,531 | 3/1932 | Taylor | 2/174 |
| 2,148,838 | 2/1939 | Roos | 2/174 |
| 2,162,608 | 6/1939 | Davis | 2/174 |
| 2,226,956 | 12/1940 | Womack | 2/174 |
| 2,258,929 | 10/1941 | Graves | 2/174 |
| 2,296,078 | 9/1942 | Young | 2/174 |
| 2,447,215 | 8/1948 | Stovall | 2/174 |
| 2,600,392 | 6/1952 | Cancell | 2/174 |
| 3,235,882 | 2/1966 | Coleman | 2/174 |
| 3,319,262 | 5/1967 | Lee | 2/174 |
| 3,452,365 | 7/1969 | Wallace | 2/209 |
| 4,133,052 | 1/1979 | Hodgman et al. | 2/209 |
| 4,630,317 | 12/1986 | Brown et al. | 2/195.1 |
| 4,916,758 | 4/1990 | Jordan-Ross | 2/174 |
| 5,023,954 | 6/1991 | Lyons | 2/174 |
| 5,038,412 | 8/1991 | Cionni | 2/209 |
| 5,046,195 | 9/1991 | Koritan | 2/195.1 |

FOREIGN PATENT DOCUMENTS 510419  8/1939  United Kingdom .................. 2/209

*Primary Examiner*—Amy B. Vanatta
*Attorney, Agent, or Firm*—Joseph N. Breaux

[57] ABSTRACT

A skin heat shielding system comprising an elastic headband member positionable about the head of a user; a forehead shielding member constructed from a heat resistance plastic having a first headband attachment portion and a forehead shielding portion extending outwardly from the headband attachment portion, the first headband attachment portion being detachably securable to a first headband section of the headband member with a first detachable fastening mechanism; a neck shielding member constructed from a heat resistance plastic having a second headband attachment portion and a neck shielding portion extending outwardly from the headband attachment portion at an angle of less than sixty degrees, the second headband attachment portion being detachably securable to a second section of the headband member with a second detachable fastening mechanism; and a pair of ear shield members each having a fabric outer shell that is impregnated with metallic particles and that forms an internal compartment that is accessible through an elasticized opening, a heat insulating inner shell secured within the internal compartment of the outer shell having an ear receiving compartment formed therein that is sized to receive therein the ear of a user.

16 Claims, 2 Drawing Sheets

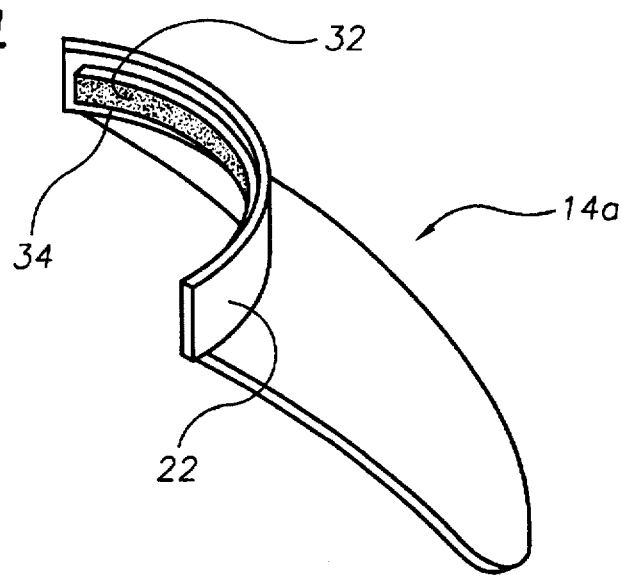
FIG. 4
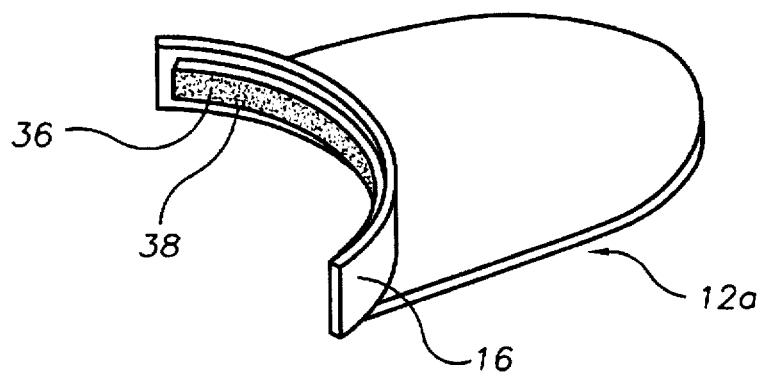
FIG. 5
FIG. 6
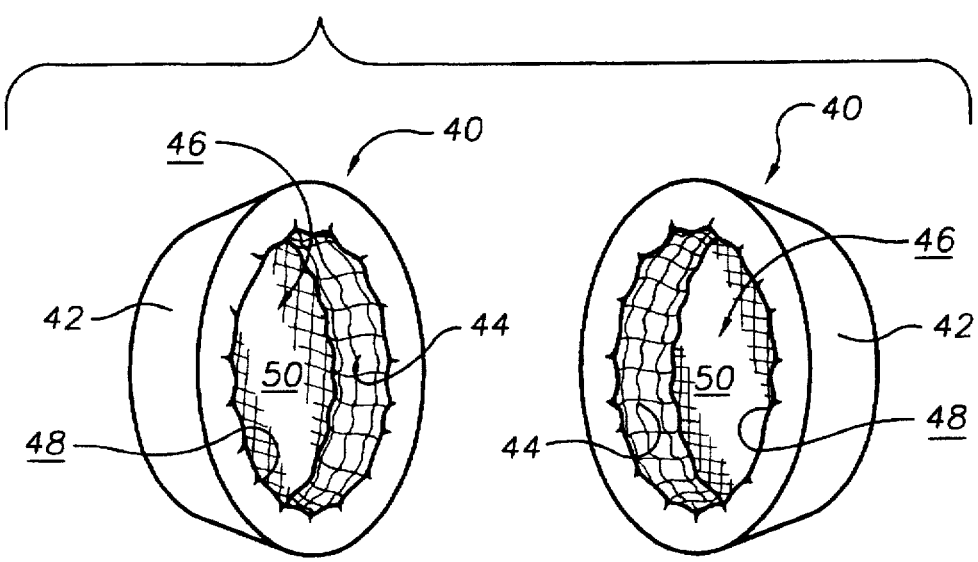

SKIN HEAT SHIELD SYSTEM

DESCRIPTION

1. Technical Field

The present invention relates to heat shields utilized to shield the skin of a person from a heat source and more particularly to a system of heat shields utilized to protect the forehead, neck and ears of person while having heat treatments on their hair.

2. Background Art

It is often necessary to apply heat to the hair of an individual when performing hair care procedures such as curling or drying. While the application of heat to the hair is necessary it is uncomfortable for the person receiving the hair care treatment to receive heat on the forehead, neck and ears. It would be desirable, therefore, to have a system for shielding the forehead, neck and ears of a person from heat resulting from receiving hair care treatments such as curling and drying. For sanitary purposes it would also be desirable if the shielding system could be disinfected and reused.

GENERAL SUMMARY DISCUSSION OF INVENTION

It is thus an object of the invention to provide a skin heat shield system that shields the forehead, neck and ears of a person receiving hair care treatments.

It is a further object of the invention to provide a skin heat shield system for shielding the forehead, neck and ears of a person receiving hair care treatments that may be disinfected and reused.

Accordingly, a skin heat shielding system is provided. The skin heat shielding system comprises an elastic headband member positionable about the head of a user; a forehead shielding member constructed from a heat resistance plastic having a first headband attachment portion and a forehead shielding portion extending outwardly from the first headband attachment portion, the first headband attachment portion being detachably securable to a first headband section of the headband member with a first detachable fastening mechanism; a neck shielding member constructed from a heat resistance plastic having a second headband attachment portion and a neck shielding portion extending outwardly from the second headband attachment portion at an angle of less than sixty degrees, the second headband attachment portion being detachably securable to a second section of the headband member with a second detachable fastening mechanism; and a pair of ear shield members each having a fabric outer shell that is impregnated with metallic particles and that forms an internal compartment that is accessible through an elasticized opening, a heat insulating inner shell secured within the internal compartment of the outer shell having an ear receiving compartment formed therein that is sized to receive therein the ear of a user.

BRIEF DESCRIPTION OF DRAWINGS

For a further understanding of the nature and objects of the present invention, reference should be had to the following detailed description, taken in conjunction with the accompanying drawings, in which like elements are given the same or analogous reference numbers and wherein:

FIG. 4 is a perspective view of the exemplary neck shield member in isolation showing a second portion of a preferred second attachment mechanism.

FIG. 5 is a perspective view of the exemplary forehead shield member in isolation showing a second portion of a preferred first attachment mechanism.

FIG. 6 is a perspective view of an exemplary pair of ear shield members showing the fabric outer shell, the internal compartment, the elasticized opening into the internal compartment, and the heat insulating inner shell.

EXEMPLARY MODE FOR CARRYING OUT THE INVENTION

As discussed herein before, the skin heat shielding system of the present invention comprises an elastic headband member positionable about the head of a user; a forehead shielding member securable to a first headband section of the headband member; a neck shielding member securable to a second section of the headband member; and a pair of ear shield members.

Figure 1:
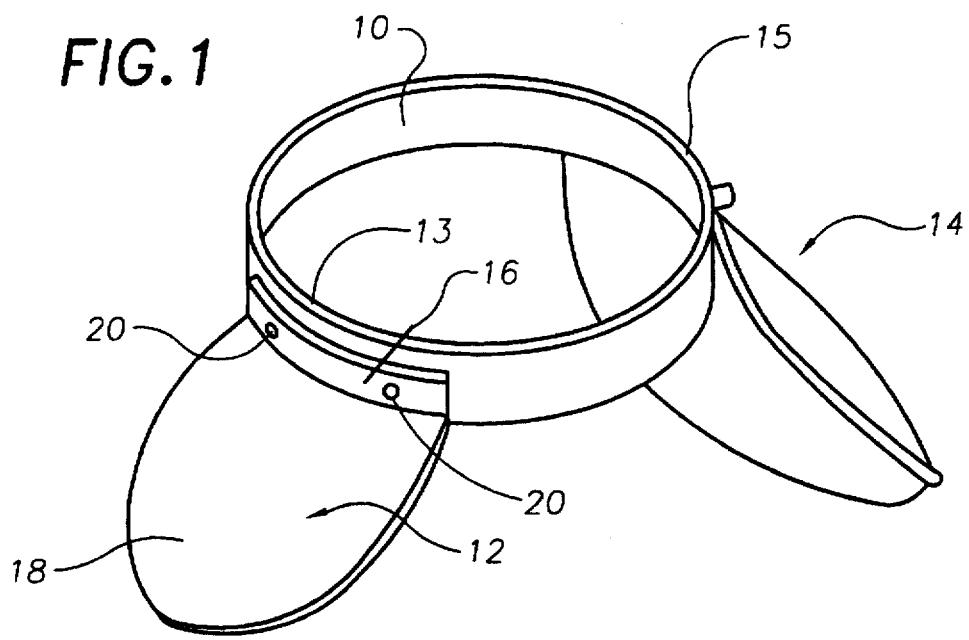
FIG. 1 is a perspective view of an exemplary elastic headband member with an exemplary forehead shielding member secured to a first section of the headband member and an exemplary neck shielding member secured to a second section of the headband member.

FIG. 1 shows an exemplary elastic headband member 10 with an exemplary forehead shielding member, generally designated by the numeral 12, secured to a first section 13 of headband member 10 and an exemplary neck shielding member, generally designated by the numeral 14, secured to a second section 15 of headband member 10.

Headband member 10 is a closed loop of cotton fabric having an elastic band stitched therein. Headband member 10 is sized to fit over the head of a user and to be comfortably positioned with first section 13 positioned on the forehead of the wearer and second section 15 positioned on the back of the wearer's neck just below the hairline. Headband member 10 can be laundered to disinfect and remove perspiration stains and the like after each use.

In this embodiment, forehead shielding member 12 is molded from heat resistant nylon and has a first headband attachment portion 16 that is curved to follow the forehead of a wearer and a forehead shielding portion 18 that extends outwardly from first headband attachment portion 16. First headband attachment portion 16 is detachably secured to first section 13 with a pair of snaps 20 that allow forehead shielding member 12 to be removed from headband member 10 prior to laundering. Forehead shielding member 12 can be cleaned and disinfected after each use by wiping with a disinfectant cleaning solution or agent.

Figure 2:
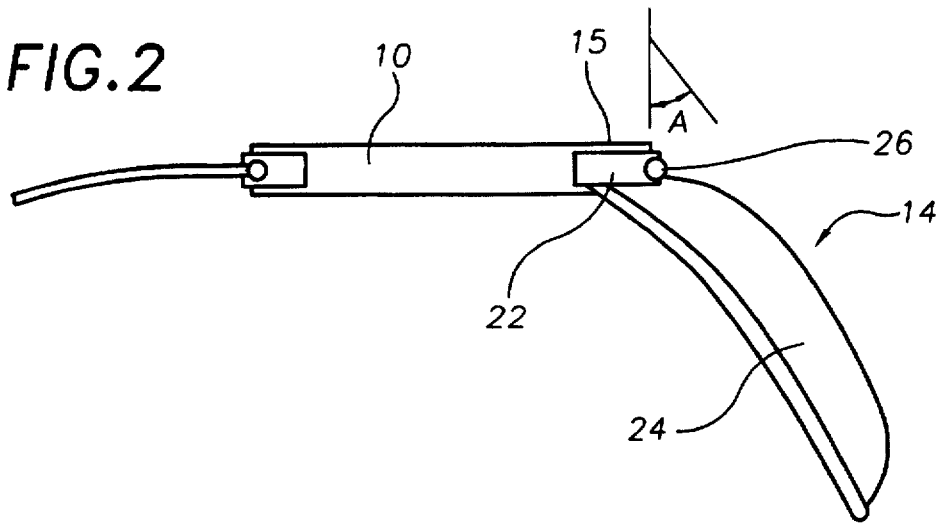
FIG. 2 is a side view of the exemplary elastic headband member, forehead shield member and neck shield member showing the neck shielding portion extending from the second attachment portion at an angle of forty-five degrees and the use of snaps as the first and second detachable connecting mechanism.

Neck shielding member 14 is also molded from heat resistant nylon. With reference to FIG. 2, neck shielding member 14 has a second headband attachment portion 22 and a neck shielding portion 24 that extends outwardly from second headband attachment portion 22 at an angle "A" of about forty-five degrees. Second headband attachment portion 22 is detachably secured to second section 15 of headband member 10 with a second pair of snap fasteners 26 (only one shown). Neck shielding member 14 is removed from headband member 10 prior to laundering. Neck shielding member 14 can also be cleaned and disinfected after each use by wiping with a disinfectant cleaning solution or agent.

Figure 3:
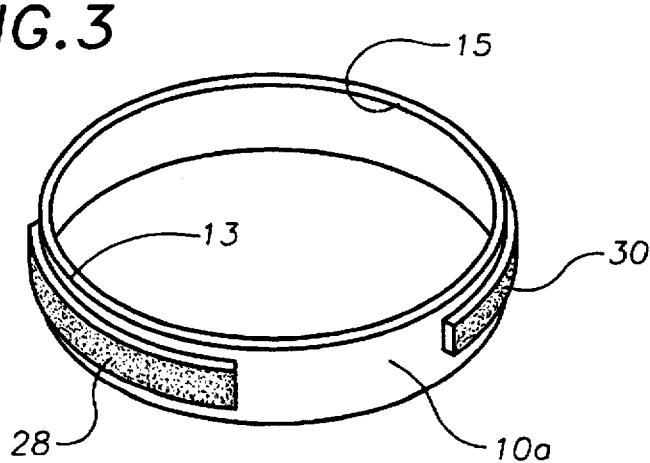
FIG. 3 is a perspective view of the elastic headband member in isolation showing a portion of a preferred first and second attachment mechanism.

FIG. 3 shows a second exemplary headband member 10a having a first section 28 of loop material from a hook and pile fastener stitched to first section 13 and a third section 30 of loop material from a hook and pile fastener stitched to second section 15. FIG. 4 shows a second exemplary neck shield member 14a that is identical to neck shield member 14 except a fourth section 32 of hook material from a hook and pile fastener is glued to the internally curved portion 34 of second headband attachment portion 22. Neck shield member 14a is detachably securable to headband member 10a by contacting fourth section 32 and third section 30.

FIG. 5 shows a second exemplary forehead shield member 12a that is identical to forehead shield member 12 except a second section 36 of hook material from a hook and pile fastener is glued to the internally curved portion 38 of first headband attachment portion 16. Forehead shield member 12a is detachably securable to headband member 10a by contacting second section 36 and first section 28.

FIG. 6 shows an exemplary identical pair of ear shield members, each generally designated by the numeral 40. Each ear shield member 40 includes a fabric outer shell 42 and a heat insulating inner shell 44. Fabric outer shell 42 is impregnated with aluminum particles and coated with a temperature resistant plastic resin. Fabric outer shell 42 forms an internal compartment 46 that is accessible through an elasticized opening 48. Heat insulating inner shell 44 is formed from quilted cotton batting and is secured within internal compartment 46 by the elastic force of elasticized opening 48. Heat insulating inner shell 44 includes an internal ear receiving compartment 50 that is sized to allow the ear of a user to be positioned therein and shielded from heat.

Use of the skin heat shielding system is now described with general reference to FIGS. 1–6. The system is donned by placing an ear shield 40 onto each ear of the user by inserting each ear through an elasticized opening 48 and positioning the outer ear into internal ear receiving compartment 50. Constriction of elasticized opening 48 around the outer ear keeps each ear shield 40 in place. Forehead shield member 12 and neck shield member 14 are then secured to headband member 10 as previously described and headband member 10 placed over the head. First section 13 is then placed against the forehead of the user and second section 15 is placed against the back of the user's neck just below the hairline. The system is now in place and the user can comfortably sit beneath a hair dryer or receive curling treatments while protected by forehead shielding member 12, neck shielding member 14 and the two ear shielding members 40. After the hair treatment is finished, the skin shielding system can be removed by reversing the previous steps. Headband member 10 and both ear shielding members 40 can then be laundered and forehead shielding member 12 and neck shielding member 14 cleaned and disinfected in the manner previously described.

It can be seen from the preceding description that a system for shielding the forehead, neck and ears of a person from heat resulting from receiving hair care treatments such as curling and drying has been provided that can be disinfected and reused.

It is noted that the embodiment of the skin heat shield system described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A skin heat shield system comprising:

an elastic headband member positionable about a head of a user;

a forehead shielding member constructed from a heat resistant plastic having a first headband attachment portion and a forehead shielding portion extending outwardly from said headband attachment portion, said first headband attachment portion being detachably securable to a first headband section of said headband member with a first detachable fastening mechanism;

a neck shielding member constructed from a heat resistant plastic having a second headband attachment portion and a neck shielding portion extending outwardly from said headband attachment portion at an angle of less than sixty degrees, said second headband attachment portion being detachably securable to a second section of said headband member with a second detachable fastening mechanism; and a pair of ear shield members each having a fabric outer shell that is impregnated with metallic particles and that forms an internal compartment that is accessible through an elasticized opening, a heat insulating inner shell secured within said internal compartment of said outer shell having an ear receiving compartment formed therein that is sized to receive therein an ear of a user.

2. The skin heat shield system of claim 1, wherein:

said first detachable fastening mechanism includes a first fastener portion secured to said first headband attachment portion of said forehead shielding member and a second fastener portion secured to said first section of said headband member, said first and second fastener portions being connectable to secure said forehead shielding member to said headband member; and said second detachable fastening mechanism includes a third fastener portion secured to said second headband attachment portion of said neck shielding member and a fourth fastener portion secured to said second section of said headband member with a second detachable fastening mechanism, said third and fourth fastener portions being connectable to secure said neck shielding member to said headband member.

3. The skin heat shield system of claim 2, wherein:

said first and second detachable fastening mechanisms are hook and pile fasteners.

4. The skin heat shield system of claim 2 wherein:

said first and second detachable fastening mechanisms are snap fasteners.

5. The skin heat shield system of claim 1 wherein:

said neck shielding member is molded from nylon; and said forehead shielding member is molded from nylon.

6. The skin heat shield system of claim 1 wherein:

said fabric outer shell is impregnated with aluminum particles and a heat resistant plastic resin.

7. The skin heat shield system of claim 2 wherein:

said neck shielding member is molded from nylon; and said forehead shielding member is molded from nylon.

8. The skin heat shield system of claim 2 wherein:

said fabric outer shell is impregnated with aluminum particles and a heat resistant plastic resin.

9. The skin heat shield system of claim 3 wherein:
said neck shielding member is molded from nylon; and
said forehead shielding member is molded from nylon.

10. The skin heat shield system of claim 3 wherein:
said fabric outer shell is impregnated with aluminum particles and a heat resistant plastic resin.

11. The skin heat shield system of claim 9 wherein:
said fabric outer shell is impregnated with aluminum particles and a heat resistant plastic resin.

12. The skin heat shield system of claim 4 wherein:
said neck shielding member is molded from nylon; and
said forehead shielding member is molded from nylon.

13. The skin heat shield system of claim 4 wherein:
said fabric outer shell is impregnated with aluminum particles and a heat resistant plastic resin.

14. The skin heat shield system of claim 12 wherein:
said fabric outer shell is impregnated with aluminum particles and a heat resistant plastic resin.

15. The skin heat shield system of claim 7 wherein:
said fabric outer shell is impregnated with aluminum particles and a heat resistant plastic resin.

16. The skin heat shield system of claim 5 wherein:
said fabric outer shell is impregnated with aluminum particles and a heat resistant plastic resin.

* * * * *